(12) United States Patent
Taylor et al.

(10) Patent No.: US 9,549,905 B2
(45) Date of Patent: Jan. 24, 2017

(54) TREATMENT OF INFLAMMATORY AND INFECTIOUS SKIN DISORDERS

(75) Inventors: Emma Taylor, Santa Monica, CA (US); Jackson Thomas S. Champer, Monrovia, CA (US); Jenny J. Kim, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/006,910

(22) PCT Filed: Mar. 23, 2012

(86) PCT No.: PCT/US2012/030335
§ 371 (c)(1),
(2), (4) Date: Sep. 23, 2013

(87) PCT Pub. No.: WO2012/129499
PCT Pub. Date: Sep. 27, 2012

(65) Prior Publication Data
US 2014/0018437 A1 Jan. 16, 2014

Related U.S. Application Data

(60) Provisional application No. 61/466,510, filed on Mar. 23, 2011.

(51) Int. Cl.
| | | |
|---|---|---|
| *A61K 31/327* | (2006.01) | |
| *A61K 31/05* | (2006.01) | |
| *A61K 45/06* | (2006.01) | |
| *A61K 31/065* | (2006.01) | |
| *A61K 31/203* | (2006.01) | |
| *A61K 31/343* | (2006.01) | |
| *A61K 31/355* | (2006.01) | |
| *A61K 31/395* | (2006.01) | |
| *A61K 31/4436* | (2006.01) | |
| *A61K 31/7004* | (2006.01) | |
| *A61K 9/00* | (2006.01) | |

(52) U.S. Cl.
CPC ............. *A61K 31/05* (2013.01); *A61K 9/0014* (2013.01); *A61K 31/065* (2013.01); *A61K 31/203* (2013.01); *A61K 31/327* (2013.01); *A61K 31/343* (2013.01); *A61K 31/355* (2013.01); *A61K 31/395* (2013.01); *A61K 31/4436* (2013.01); *A61K 31/7004* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,781,410 B2 | 8/2010 | Saliou | |
| 2008/0032938 A1* | 2/2008 | Saliou et al. | 514/25 |
| 2008/0206155 A1* | 8/2008 | Tamarkin et al. | 424/44 |
| 2009/0005439 A1 | 1/2009 | Faryniarz | |
| 2009/0093440 A1* | 4/2009 | Murad | 514/55 |
| 2010/0310680 A1 | 12/2010 | Chen et al. | |

FOREIGN PATENT DOCUMENTS

| | | |
|---|---|---|
| CN | 101500551 A | 8/2009 |
| KR | 20020085307 A1 | 11/2002 |
| WO | 2007110883 A1 | 10/2007 |
| WO | 2008019212 A1 | 2/2008 |
| WO | 2011039175 A1 | 4/2011 |

OTHER PUBLICATIONS

Docherty et al. (Journal of Antimicrobial Chemotherapy (2007) 59, 1182-1184).*
Docherty, et al., "Resveratrol Inhibition of Propionibacterium acnes (abstract)", 2007, pp. 1182-1184, vol. 59, No. 6, Publisher: J. Antimicrob. Chemother.
Stivala et al., "Specific Structural Determinants Are Responsible for the Antioxidant Activity and the Cell Cycle Effects of Resveratrol", Jun. 22, 2001, pp. 22586-22594, vol. 276, No. 25, Publisher: The Journal of Biological Chemistry.
Farris, "Idebenone, green tea, and Coffeeberry extract: new and innovative antioxidants (abstract)", 2007, pp. 322-329, vol. 20, No. 5, Publisher: Dermatol. Ther.
Johnson, et al., "Use of Systemic Agents in the Treatment of Acne Vulgaris", 2000, pp. 1823-1830, vol. 62, No. 8, Publisher: Am. Fam. Physician.
Robert J. MacNeal, "Treatment of Skin Disorders", Jul. 3, 2012, Publisher: http://www.merckmanuals.com/home/skin_disorders/diagnosis_and_treatment_of_skin_disorders/treatment_of_skin_disorders.html.
Goodfellow, et al., "Oral spironolactone improves acne vulgaris and reduces sebum excretion (abstract)", 1984, pp. 209-214, vol. 111, No. 2, Publisher: Br. J. Dermatol.
"International Preliminary Report on Patentability received in PCT/US2012/030335, mailed Sep. 24, 2013".
"Written Opinion received in PCT/US2012/030335, mailed Aug. 16, 2012".

(Continued)

*Primary Examiner* — Kortney L Klinkel
*Assistant Examiner* — William Lee
(74) *Attorney, Agent, or Firm* — Suzannah K. Sundby, Esq.; Canady + Lortz LLP

(57) ABSTRACT

Disclosed herein is a composition comprising of resveratrol and/or derivatives thereof and/or functionally related compounds and benzoyl peroxide and/or derivatives thereof and/or functionally related compounds for the treatment of acne and other inflammatory or infectious skin disorders. Also disclosed are methods of treating acne and other inflammatory and infectious skin disorders using the compositions described herein.

21 Claims, 7 Drawing Sheets

(56) References Cited

OTHER PUBLICATIONS

Office Action received in CN 2012800247535, mailed Oct. 31, 2014.

Second Office Action received in CN2012800247535, mailed Jun. 19, 2015.

* cited by examiner

TREATMENT OF INFLAMMATORY AND INFECTIOUS SKIN DISORDERS

CROSS REFERENCE TO RELATED APPLICATIONS

This application claims the benefit under 35 U.S.C. §371 of International Application Number PCT/US12/030335, filed Mar. 23, 2012, which claims priority under 35 U.S.C. §119(e) to U.S. provisional application Ser. No. 61/466,510, filed Mar. 23, 2011, the entire contents of which are incorporated herein by reference.

BACKGROUND OF THE INVENTION

Acne affects up to 85% of adolescents and causes significant morbidity.[1] Topical therapy is the first line treatment for mild acne and can be used as adjunctive therapy for moderate to severe acne. However, undesirable side effects such as dryness, redness, and irritation from topical therapies such as tretinoin derivatives and benzoyl peroxide limit patient compliance.[1,2,3,4,5]

Acne pathogenesis is mediated by several factors including hyperproliferation and abnormal differentiation of keratinocytes, impaction of follicles forming a keratinaceous plug, increased androgens and sebum production, *Propionibacterium acnes* overgrowth, and the production of proinflammatory mediators.[6]

There remains a need to identify novel acne regimens and adjuvant therapies to address the limitations of current topical therapies.

SUMMARY

Figure 1A:
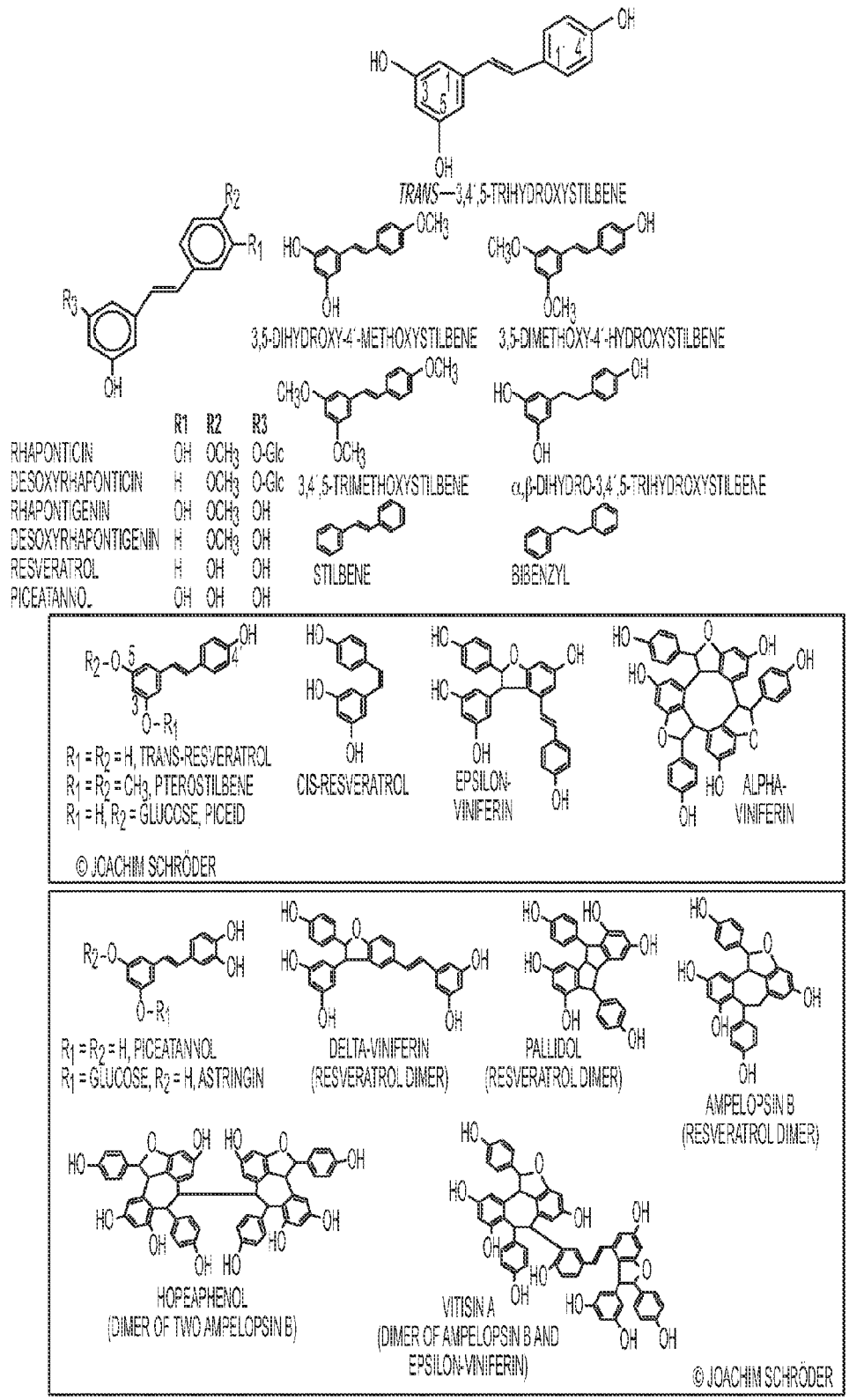
FIG. 1A. Resveratrol and non-limiting examples of its derivatives.

The present invention relates to a composition comprising a pharmaceutically effective amount of resveratrol and/or derivative(s) thereof and/or functionally related compound(s) alone or in various combinations with a pharmaceutically effective amount of benzoyl peroxide and/or its derivative(s) and/or functionally related compound(s), which include but are not limited to, antioxidants, topical retinoids, topical antibiotics, oral antiacne agents, oral antibiotics, topical acids, topical antifungals, in addition to solubilizers, suspending agents, preservatives, non-ionic surfactants, humectants, emulsifiers, emollients, fragrances, and water for the treatment of acne and other inflammatory and infectious skin disorders. In certain embodiments, a provided composition is formulated for topical use. In certain embodiments, a provided composition is formulated for oral use. In certain embodiments, a provided composition comprises trans-resveratrol. In certain embodiments, a provided composition comprises trans-resveratrol and benzoyl peroxide.

In some embodiments, a composition comprising resveratrol and/or derivative(s) thereof and/or functionally related compound(s) in combination with benzoyl peroxide and/or its derivative(s) and/or functionally related compound(s)-containing may contain one or more additional beneficial agents. In certain embodiments, beneficial agents include nutrients and/or vitamins.

The present invention also relates to a method of treating, improving the appearance of, and/or preventing acne including, but not limited to mild, moderate, severe, comedonal, inflammatory, pustular, or cystic acne in a human patient comprising administering to the patient a composition comprising resveratrol and/or derivative(s) thereof and/or functionally related compound(s) which may also include pharmaceutically effective compounds such as benzoyl peroxide and/or its derivative(s) and/or functionally related compound(s). In some embodiments, a provided method comprises topical administration of a provided composition. In some embodiments, a provided method comprises oral administrated of a provided composition. In certain embodiments, a provided composition is administered via one or multiple doses applied to the skin and/or taken orally daily.

In some embodiments, the present invention provides a method of treating, improving the appearance of, and/or preventing an inflammatory skin disease, including, but not limited to rosacea, seborrheic dermatitis, perioral dermatitis, pseudofolliculitis barbae in a human patient comprising administering to the patient a composition comprising resveratrol and/or derivative(s) thereof and/or functionally related compound(s) which may include one or more additional pharmaceutically effective compounds such as benzoyl peroxide and/or its derivative(s) and/or functionally related compound(s). In some embodiments, a provided method comprises topical administration of a provided composition. In some embodiments, a provided method comprises oral administrated of a provided composition. In certain embodiments, a provided composition is administered via one or multiple doses applied to the skin and/or taken orally daily.

In some embodiments, the present invention provides a method of treating, improving the appearance of, and/or preventing other infectious skin diseases including, but not limited to folliculitis, tinea, and onychomycosis in a human patient comprising administering to the patient a composition comprising resveratrol and/or derivative(s) thereof and/or functionally related compound(s) which may include one or more additional pharmaceutically effective compounds such as benzoyl peroxide and/or its derivative(s) and/or functionally related compound(s). In some embodiments, a provided method comprises topical administration of a provided composition. In some embodiments, a provided method comprises oral administrated of a provided composition. In certain embodiments, a provided composition is administered via one or multiple doses applied to the skin and/or taken orally daily.

Another aspect of the present invention relates to the use of resveratrol and/or derivative(s) thereof and/or functionally related compound(s) optionally in combination with one or more pharmaceutically effective compounds such as benzoyl peroxide and/or derivative(s) thereof and/or functionally related compound(s) in the manufacture of a medicament for treating, improving the appearing of, and/or preventing acne and other inflammatory or infectious skin diseases as described herein.

The present invention relates to a method of treating, improving the appearance of, and/or preventing acne and other inflammatory and infectious skin disorders as described herein, which comprises administering orally and/or topically one or multiple doses of a composition comprising resveratrol and/or derivative(s) thereof and/or functionally related compound(s) which may include pharmaceutically effective compounds such as benzoyl peroxide and/or its derivative(s) and/or functionally related compound(s).

Topical compositions according to the present invention may be formulated, for example, in a cream, ointment, lotion, gel, foam, solution, or cleanser form.

Oral compositions according to the present invention may be formulated, for example, in a pill, syrup, liquid solution, powder, or gel form.

DEFINITIONS

The term "active ingredient", as used herein, refers to resveratrol and/or derivative(s) thereof and/or functionally related compound(s) optionally in combination with benzoyl peroxide and/or its derivative(s) and/or functionally related compound(s). Resveratrol derivatives include but are not limited to cis-3,4'5-trihydroxystilbene, 3,4-dihydroxy-4'methoxystilbene, 3,5-dimethoxy-4'-hydroxystilbene, 3,4', 5-trimethoxystilbene, α,β-dihydro-3,4',5-trihydroxystilbene, cis-piceid, trans-piceid, pterostilbene, epsilon-viniferin, alpha-viniferin, delta-viniferin, resveratrol dimer, 5,4'-dihydroxy-3-O-methoxystilbene, 3,4-dihydroxy-4'-O-methoxystilbene, resveratroloside, and other known or as yet undiscovered derivatives that may arise when substituting different functional R groups (where R may be, for example, hydrogen, methyl, $C_{1-6}$ alkyl, hydroxy, or $C_{1-6}$ alkoxy) at one or more various positions around the central core benzene rings. Resveratrol is an antioxidant, and functionally related compounds comprise other antioxidants including but not limited to ascorbic acid (vitamin C), α-tocopherol (vitamin E), polyphenols, lipoic acid, glutathione, uric acid, carotenes, ubiquinol (coenzyme Q), green tea extract, and/or coffee berry extract. Benzoyl peroxide's parent compound includes benzoic acid. It is considered a peroxide agent because it contains an oxygen-oxygen single bond. Other topical peroxides (e.g., benzoyl peroxide derivatives) include but are not limited to hydrogen peroxide, which also has antimicrobial properties, and can be added to or substituted for benzoyl peroxide in the compositions described herein. Benzoyl peroxide is a known acne medication, antibiotic and antifungal. Functionally related compounds include but are not limited to topical antiacne treatments including but not limited to topical retinoids (retinol, adapalene, tretinoin, and tazarotene), azelaic acid, salicylic acid, glycolic acid, oral antiacne agents including spironolactone, isotretinoin and oral antibiotics including doxycycline, tetracycline, minocycline, topical antibiotics including but not limited to clindamycin, erythromycin, sulfacetamide sodium/sulfur, silver sulfadiazine, neomycin, polymyxin B, and bacitracin, mupirocin, and retapamulin, and topical antifungals including but not limited to ketoconazole, miconazole, fluconazole, clotrimazole, undeclyenic acid, sertaconazole, terbinifine, butenafine, clioquinol, haloprogin, nystatin, naftitine, tolnaftate, ciclopirox, amphotericin B, and tea tree oil.

Resveratrol and/or derivative(s) thereof and/or functionally related compound(s) in combination with benzoyl peroxide and/or its derivative(s) and/or functionally related compound(s) may be utilized as a mixture of resveratrol and/or derivative(s) thereof and/or functionally related compound(s) in combination with benzoyl peroxide and/or its derivative(s) and/or functionally related compound(s) varying combinations of the active ingredients each ranging from 0.00005%-75% of the total formula, with more expected ranges for each active ingredient ranging from 0.05-20% of the total formula.

The term "solubilizer" and/or "solubilizer phase" as used herein refers to compound or mixture of compounds in which the resveratrol and/or derivatives thereof and/or functionally related compounds in combination with benzoyl peroxide and/or its derivatives and/or functionally related compounds are initially dissolved. The solubilizer phase is preferably a mixture of water miscible organic compounds and solubilizers may include but not limited to surfactants polysorbate 80 and cetyl acetate, cetyl alcohol, stearyl alcohol, ceostearyl alcohol, oleyl alcohol, polyoxyethylene glycol (PEG), polypropylene glycol, glucoside alkyl ethers, triton X-100, glycerol alkyl esters, sorbitan, DMSO The term "emulsifier" as used herein refers to a compound or a mixture of compounds that helps the suspending agents combine with the other ingredients namely resveratrol and/or derivatives thereof and/or functionally related compounds in combination with benzoyl peroxide and/or its derivatives and/or functionally related compounds, and include, without limitation stearyl alcohol, polysorbate 60, steareth-20, Irish moss The terms "suspending agent(s)" as used herein refers to organic compounds that suspend the pre-dissolved resveratrol and/or derivatives thereof and/or functionally related compounds in combination with benzoyl peroxide and/or its derivatives and/or functionally related compounds before being dispersed in water. Suspending agents, include, without limitation olive oil, shea butter, cocoa butter, vegetable oil and the like.

The term "preservative(s)" as used herein refers to compounds that reduce the growth of fungus and other bacterial agents and include, without limitation tinosan, potassium sorbate, grapefruit seed extract, and the class of paraben compounds and the like.

The term "non-ionic surfactant(s)" as used herein refers to compounds which act at the water-air and water-oil interfaces, thereby enhancing wetting ability, emulsion, stabilization, foaming, rheology, antistatic, lubricity, and surface conditioning properties of the formula and include, without limitation lanolin, cetyl alcohol, stearyl alcohol, ceostearyl alcohol, oleyl alcohol, polyoxyethylene glycol (PEG), polypropylene glycol, glucoside alkyl ethers, triton X-100, glycerol alkyl esters, sorbitan and the like.

The term "emollient(s)" as used herein refers to compounds that soften the skin smooth by preventing skin from loosing moisture and include, without limitation candellilla wax, sweet almond oil, apricot oil, emu oil, argan oil, glycerin, coconut oil, grape seed oil, honey, lanolin and the like.

The term "fragrance(s)" as used herein refers to chemicals added to give an aroma to the formulation and include but are not limited to essential oils and the like.

In general, an "effective amount" of an active agent (e.g., a therapeutic agent, composition, and/or formulation) refers to an amount sufficient to elicit the desired biological response. In some embodiments, an effective amount of a substance is an amount that is sufficient, when administered to a subject suffering from or susceptible to a disease, disorder, and/or condition, to treat, prevent, and/or delay the onset of one or more symptoms of the disease, disorder, and/or condition. As will be appreciated by those of ordinary skill in this art, an effective amount of a substance may vary depending on such factors as the desired biological endpoint, the substance to be delivered, the pharmacokinetics of the compound, the target cell or tissue, the disease being treated, the mode of administration, and the patient, etc. For example, an effective amount of a composition and/or formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. Those of ordinary skill in the art will appreciate that, commonly, an effective amount will be administered over a series of individual doses. In some embodiments, the term "effective amount" when used in a pharmaceutical context (e.g., pharmaceutically effective amount) means that an agent is present in an amount sufficient to achieve a desired therapeutic effect. In some embodiments, the term "effective amount" when used in a cosmetic context (e.g., cosmetically effective amount) means that an agent is present in an amount sufficient to achieve an aesthetic effect. In some embodiments, the term "effective amount" when used in a cosmeceutical context (e.g., cosmeceutically effective amount) means that an agent is present in an amount sufficient to achieve a therapeutic and/or aesthetic effect. In some embodiments, a composition may be considered to contain or deliver an effective amount of a relevant agent if it contains or delivers an appropriate dose for use in a therapeutic regimen that achieves a therapeutic result when administered to an individual or when it is statistically likely to achieve a therapeutic result in when administered to a population (e.g., of individuals suffering from or susceptible to a relevant disease, disorder, or condition.

As used herein, the phrase "in combination" refers to the simultaneous administration of two or more agents to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in or on the subject's body, they are considered to be administered "in combination". In certain embodiments, two or more agents administered in combination are present in the same composition and/or formulation. In certain embodiments, two or more agent administered in combination are administered separately.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 66: 1-19, 1977; incorporated herein by reference. Such salts can be prepared in situ during the final isolation and purification of the compounds of the invention, or separately (e.g., by reacting the free base functionality with a suitable organic or inorganic acid). Alternatively or additionally, salts may form during formulation of a compound. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

As used herein, the terms "treat," "treating" and "treatment," refer to an action that occurs while a patient is suffering from or susceptible to a specified disease, disorder or condition, which delays onset of and/or reduces the frequency or severity of one or more symptoms or features of the disease disorder or condition. Thus, "treat", "treating", and "treatment" refer to any type of treatment that imparts a benefit to a subject afflicted with a disease, disorder or condition, including improvement in the condition of the subject (e.g., in one or more symptoms), delay in the progression of the disease, disorder or condition, prevention or delay of the onset of the disease, disorder or condition, etc.

The expression "unit dosage form" as used herein refers to a physically discrete unit of a provided formulation appropriate for the subject to be treated. It will be understood, however, that the total daily usage of provided formulation will be decided by the attending physician within the scope of sound medical judgment. The specific effective dose level for any particular subject or organism may depend upon a variety of factors including the disorder being treated and the severity of the disorder; activity of specific active agent employed; specific formulation employed; age, body weight, general health, sex and diet of the subject; time of administration, and rate of excretion of the specific active agent employed; duration of the treatment; drugs and/or additional therapies used in combination or coincidental with specific complex(es) employed, and like factors well known in the medical arts. In some embodiments, a unit dosage form contains an amount of a therapeutically active agent appropriate for use in a therapeutic regimen (i.e., in a regimen that delivers a therapeutically effective amount of an agent). In some embodiments, such a unit dosage form may be considered to contain a "therapeutically effective amount" of an agent if it contains an amount appropriate for use in such a therapeutic regimen, even if a single dose would not be expected to be effective alone.

The terms "composition" and "formulation" are used interchangeably herein.

DETAILED DESCRIPTION OF CERTAIN EMBODIMENTS

Resveratrol (RES), or 3,5,4'-trihydroxystilbene, is a polyphenol found in red wine, colored berries, and inedible parts of the peanut plant. Resveratrol has been shown to have a variety of therapeutic properties including antioxidant, antiinflammatory, antimicrobial, antineoplastic, and wound healing activity.[7] Studies have found RES to be one of the strongest antioxidants, stronger than Vitamin A, C, and E.[8] Antioxidants reduce lipid peroxidation and the development of reactive oxygen species, which cause tissue inflammation and DNA damage. Resveratrol is also known to have antiviral, antifungal, antibacterial, and antiprotozoal effects.[9,10,11] Its expression in grapes correlates with the amount of environmental stress and pathogenic attacks.[12] Additionally, grape seed extract, which contains RES, is made up of proanthocyanidins (condensed tannins), which have been shown to increase VEGF expression, and angiogenesis in healing wounds.[13] Lastly, RES binds to the estrogen receptor, and prior evidence suggests that wine consumption may minimize perimenopausal symptoms.[14,15] In vivo human studies in both oral and topical administration of resveratrol have shown it to be a safe and well tolerated therapy. Topical studies have also revealed that resveratrol does not increase transepidermal water loss (TEWL) or erythema, indirect measures of cutaneous safety.

Despite all these beneficial properties of RES, prior to April 2011, there were no studies evaluating its application in the treatment of acne vulgaris. Only recently, an abstract from Italy details a pilot study demonstrating the efficacy of resveratrol in the treatment of acne vulgaris.[16] Beyond this study, only one other in vitro study exists that demonstrated antimicrobial activity of RES against P. acnes, the pathogenic bacteria in acne[17] It is possible that the antimicrobial, anti-inflammatory, hormonal, and wound healing properties of RES may counteract some of the above pro-acne mediators, and make resveratrol and/or derivatives thereof a novel candidate for acne therapy and other inflammatory skin disorders such as rosacea, seborrheic dermatitis, and pseudofolliculitis, perioral dermatitis, in addition to other infectious processes such as folliculitis, impetigo, tinea, candidiasis, and onychomycosis. Resveratrol can be used either as a monotherapy or in combination with other existing acne therapies, anti-inflammatory therapies or antimicrobials and can be administered topically or orally.

Data from experiments in this study demonstrate that, not only is resveratrol effective at reducing bacterial count of P. acnes, but that there is actually enhanced bactericidal efficacy when combined with benzoyl peroxide. This was unexpected as resveratrol is an antioxidant, and in other studies, antioxidants have actually counter-acted the tumerogenic effects of benzoyl peroxide, and benzoyl peroxide has actually been shown to reduce the amount of intracellular Vitamin E specifically when added to keratinocytes.[18,19]. Resveratrol was also shown to reduce IL-12 activity in our experiments, which is a marker for inflammation, implying a potential use for resveratrol in other inflammatory processes in addition to acne.

This unexpected enhanced efficacy from the combination of resveratrol and benzoyl peroxide implies that the combination of resveratrol and/or its derivative(s) and/or functionally related compound(s) with benzoyl peroxide and/or its derivative(s) and/or functionally related compound(s), may serve as novel topical combination therapies for acne in addition to other inflammatory processes including but not limited to rosacea, perioral dermatitis, and seborrheic dermatitis, pseudofolliculitis in which benzoyl peroxide has been shown to be an effective therapy,[20,21,22,23] as well as infectious processes including but not limited to folliculitis, impetigo, tinea, candidiasis, and onychomycosis for which benzoyl peroxide has also been shown to be an effective therapy.[24,25,26,27]

The present invention relates to a topical and/or oral composition comprising an effective amount of resveratrol and/or derivative(s) thereof and/or functionally related compound(s) and optionally comprising pharmaceutically effective compounds such as benzoyl peroxide and/or its derivative(s) and/or functionally related compound(s) in addition to solubilizers, suspending agents, preservatives, non-ionic surfactants, humectants, emulsifiers, emollients, fragrances, and water for the treatment, improvement in the appearance of or prevention of acne and other inflammatory and infectious skin disorders. Other inflammatory skin disorders that may benefit from the above combination include but are not limited to rosacea, seborrheic dermatitis, pseudofolliculitis, and perioral dermatitis. Other infectious disorders that may also benefit from the above combination include but are not limited to folliculitis, impetigo, tinea, candidiasis, and onychomycosis.

Resveratrol and/or its derivative(s) and/or functionally associated compound(s) when combined with benzoyl peroxide and/or its derivative(s) and/or functionally related compound(s) has been shown to be effective monotherapies in inflammatory and infectious processes described herein. However, unexpectedly, our data demonstrate that the combination of resveratrol and benzoyl peroxide has a superior effect than either compound alone. These data imply that a composition comprising resveratrol and/or its derivative(s) and/or functionally associated compound(s) and benzoyl peroxide and/or its derivative(s) and/or functionally related compound(s) formulation may be even more efficacious in the therapy of acne in addition to many of the inflammatory and infectious skin disorders described herein than treatment with resveratrol or benzoyl peroxide alone.

Resveratrol derivatives include but are not limited to cis-3,4',5-trihydroxystilbene, 3,4-dihydroxy-4'methoxystilbene, 3,5-dimethoxy-4'-hydroxystilbene, 3,4'5-trimethoxystilbene, α,β-dihydro-3,4',5-trihydroxystilbene, cis-piceid, trans-piceid, pterostilbene, epsilon-viniferin, alpha-viniferin, delta-viniferin, resveratrol dimer, 5,4'-dihydroxy-3-O-methoxystilbene, 3,4-dihydroxy-4'-O-methoxystilbene, resveratroloside, and other as yet undiscovered derivatives that may arise when substituting different functional R groups (where R may be, for example, hydrogen, methyl, $C_{1-6}$ alkyl, hydroxy, or $C_{1-6}$ alkoxy) at one or more various positions around the central core benzene rings.

Resveratrol is an antioxidant, and functionally related compounds therefore comprise of other antioxidants including but not limited to Ascorbic acid (Vitamin C), α-tocopherol (Vitamin E), polyphenols, lipoic acid, glutathione, uric acid, carotenes, ubiquinol (coenzyme Q), green tea extract, and coffee berry extract. Studies have validated the use of other antioxidants in acne, such as green tea extract.[28]

Benzoyl peroxide's parent compound includes benzoic acid. It is considered a peroxide agent because it contains an oxygen-oxygen single bond. Other topical peroxides include but are not limited to hydrogen peroxide, which also has antimicrobial properties, and can be added to or substituted for benzoyl peroxide in the aforementioned combinations.

Benzoyl peroxide is a known acne medication, antibiotic and antifungal. Therefore functionally related compounds include but are not limited to topical antiacne treatments including but not limited to topical retinoids (retinol, adapalene, tretinoin, and tazarotene), oral antiacne agents including but not limited to oral antibiotics (tetracycline, doxycycline, minocycline), spironolactone, isotretinoin, topical acids (azelaic acid, salicylic acid, glycolic acid), topical antibiotics (clindamycin, erythromycin, sulfacetamide soidium/sulfur, silver sulfadiazine, neomycin, polymyxin B, and bacitracin, mupirocin, and retapamulin), and topical antifungals (ketoconazole, miconazole, fluconazole, clotrimazole, undeclyenic acid, sertaconazole, terbinifine, butenafine, clioquinol, haloprogin, nystatin, naftitine, tolnaftate, ciclopirox, amphotericin B, and tea tree oil).

The resveratrol and/or derivative(s) thereof and/or functionally related compound(s)-based combination formula, which may include aforementioned pharmaceutically effective compounds such as benzoyl peroxide and/or its derivative(s) and/or functionally related compound(s) addresses the lack of novel therapeutic options for acne vulgaris and may minimize the current issues surrounding irritating side effects of current topical and oral acne therapies, by enhancing the efficacy of active compounds, thereby allowing for a reduction in concentration of active compounds enabling a maximum therapeutic benefit with minimal side effect profile. Both topical retinoids and benzoyl peroxide, current gold standards for treating acne vulgaris have side effects such as redness, dryness, irritation, which limit patient compliance.[1,2,3,4,5] Additionally oral isotretinoin, like topical retinoids, is notorious for causing severe xerosis (dry skin) and photosensitivity, and oral antibiotics have other untoward side effects including gastrointestinal upset and photosensitivity.

The resveratrol and/or derivative(s) thereof and/or functionally related compound(s)-based combination formula, which may include aforementioned pharmaceutically effective compound(s) such as benzoyl peroxide and/or its derivative(s) and/or functionally related compound(s) addresses the lack of novel therapeutic options for rosacea, seborrheic dermatitis, perioral dermatitis, and pseudofolliculitis barbae, and may minimize the current issues surrounding irritating side effects of current topical anti-inflammatory therapies, along with potentially enhancing the efficacy of active compounds, thereby allowing for a reduction in concentration of active compounds enabling a maximum therapeutic benefit with minimal side effect profile. Topical retinoids and benzoyl peroxide products and similar oral antibiotics are commonly used for the above cutaneous conditions and have the same side effect profile and compliance issues as previously mentioned with acne therapies above.

The resveratrol and/or derivative(s) thereof and/or functionally related compound(s)-based combination formula, which may include aforementioned pharmaceutically effective compounds such as benzoyl peroxide and/or its derivative(s) and/or functionally related compound(s) addresses the lack of novel therapeutic options for cutaneous infections and may minimize the current issues surrounding the risk of contact dermatitis associated with current topical antibiotics[29], risk of microbial resistance when using topical or oral monotherapy,[30,31] along with potentially enhancing the efficacy of active compounds, thereby allowing for a reduction in concentration of active compounds enabling a maximum therapeutic benefit with minimal side effect profile.

A portion of this current invention is exemplified by the Colony-Forming Unit (CFU) assays, which compare the antibacterial activity of resveratrol to benzoyl peroxide and to a combination of resveratrol and benzoyl peroxide (See FIGS. 2A-2D). Both resveratrol and benzoyl peroxide alone are effective at reducing *Propionibacterium acnes* growth. However, the combination of resveratrol and benzoyl peroxide has a clear enhanced and sustained synergistic antimicrobial effect significantly greater than either compound alone. Thus it is evident that since prior research has shown resveratrol and benzoyl peroxide are effective monotherapies for acne, one can deduce the potential enhanced therapeutic benefit of a resveratrol and/or derivative(s) thereof and/or functionally related compound(s)-based combination formula, which may include aforementioned pharmaceutically effective compounds such as benzoyl peroxide and/or its derivative(s) and/or functionally related compounds(s). Since benzoyl peroxide is well known for having the adverse effect of causing irritation, dryness, and erythema, as mentioned above, the combination with resveratrol and/or its derivative(s) thereof and/or functionally related compound(s) may allow for a reduction in concentration of benzoyl peroxide while maintaining the same or improved efficacy. Also demonstrated from this figure is the powerful but short acting activity of benzoyl peroxide, with virtually no activity remaining after 48 hours, while resveratrol has a slow but sustained antimicrobial response. The combination being more effective early, and even after a 10 day incubation period clearly indicates an immediate and long lasting benefit of a combination resveratrol and benzoyl peroxide topical therapy.

In certain embodiments, a method according to the present invention comprises applying topically one dose or multiple doses (applications) of the resveratrol and/or derivative(s) thereof and/or functionally related compound(s)-based combination formula, which may include aforementioned pharmaceutically effective compounds such as benzoyl peroxide and/or its derivative(s) and/or functionally related compound(s) to the individual for a length of time to allow and effective amount of the active ingredient to contact, penetrate, or be absorbed by the affected skin in order to treat, improve the appearance of or prevent acne and other inflammatory and infectious skin disorders as mentioned previously.

In certain embodiments, a method according to the present invention comprises administering orally one dose or multiple doses of the resveratrol and/or derivative(s) thereof and/or functionally related compound(s)-based combination formula, which may include aforementioned pharmaceutically effective compounds such as benzoyl peroxide and/or its derivative(s) and/or functionally related compound(s) to the individual for a length of time to allow and effective amount of the active ingredient to be absorbed by the gastrointestinal system in order to treat, improve the appearance of, or prevent acne and other inflammatory and infectious skin disorders as mentioned previously.

In certain embodiments, a topical and/or oral formulation of the present invention comprises resveratrol and/or derivative(s) thereof and/or functionally related compound(s) in combination with benzoyl peroxide and/or its derivative(s) and/or functionally related compound(s). Resveratrol and/or its derivative(s) and/or functionally related compound(s), in addition to benzoyl peroxide and/or its derivative(s) and/or functionally related compound(s) may be present at varying concentrations with an expected range (at weight/volume percentage) from 0.00005% to 75% (w/v) {i.e., a 1% resveratrol, 1% benzoyl peroxide formulation would include 1 gram (g) resveratrol per 100 milliliters (ml)(1 g/100 ml) or formulation volume and 1 gram (g) benzoyl peroxide per 100 milliliters (ml)(1 g/100 ml) or formulation volume.

Figure 2A:
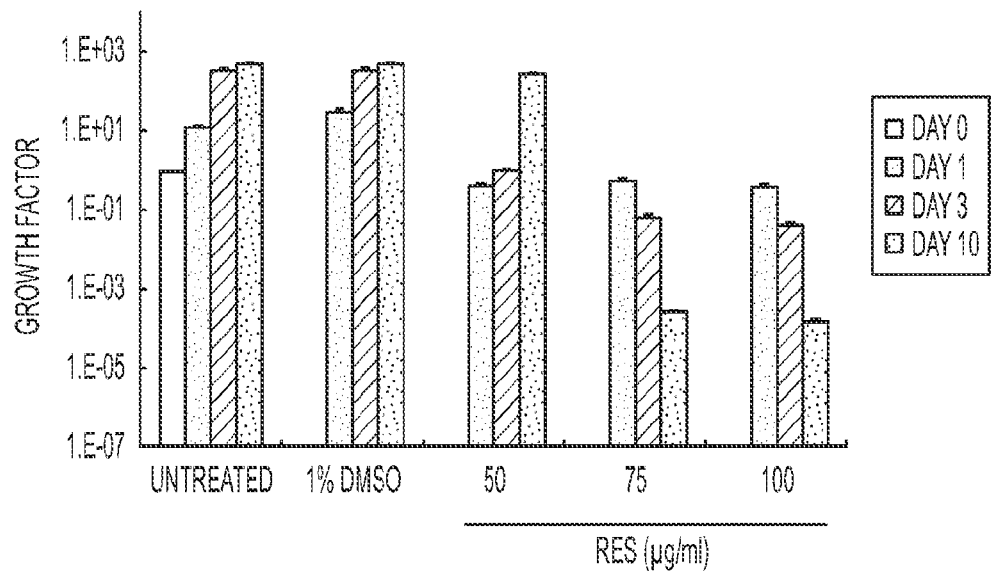
FIG. 2A. Colony Forming Unit (CFU) assays of *P. acnes* incubated with Resveratrol (RES). Bacterial growth was assessed in terms of the growth factor of *P. acnes* (Y-axis), determined by the change in the number of bacteria compared to baseline control (set at 1 on Day 0). Concentrations were obtained over a 10-day period and plotted logarithmically.

Another contemplated range for a resveratrol concentration would be from 0.00005%-0.0001% (w/v) which is further supported in FIG. 2A where 50-100 μg/ml of resveratrol was effective at reducing the amount of *P. acnes* bacteria in vitro. Another contemplated range for a benzoyl peroxide concentration would be from 0.00005%-0.0001% (w/v) which is further supported in FIG. 2B where 50-100 μg/ml of benzoyl peroxide was effective at reducing the amount of *P. acnes* bacteria in vitro. Another contemplated range for Benzoyl peroxide would include 2.5-20% (w/v) as this is the common range of percentages that exist in over the counter and prescription antiacne benzoyl peroxide products. Since our data supported the enhanced efficacy of benzoyl peroxide when combined with resveratrol, lower effective concentrations of benzoyl peroxide than have been conventionally produced are possible, (e.g. a benzoyl peroxide range of 0.05%-2.5% (w/v)).

Dosing may be varied both by changing the concentration of resveratrol and/or derivative(s) thereof and/or functionally related compound(s) and/or changing the concentration of benzoyl peroxide and/or its derivative(s) and/or functionally related compound(s), or by changing the frequency of application of the topical formulation applied to the human patient and/or changing the frequency of administering the formulation to the human patient orally. It will be evident upon review of this specification, that while a resveratrol and benzoyl peroxide-based formulation combination formulation is exemplified herein, other combinations of resveratrol derivative(s) and/or functionally related compound(s) and other benzoyl peroxide derivative(s) and/or functionally related compounds as mentioned before are also contemplated as the active ingredient(s) which will be useful to practice the present invention.

While topical dosing ranges may vary, in certain embodiments a single application (dosage) of an exemplified resveratrol and benzoyl peroxide-containing formulation of the present invention would be in the range from about 1 ml-240 ml or if in more solid form 1 g-30 grams to cover the affected areas of the body (with 30 grams representative of the average amount needed to cover the entire body).

While oral dosing ranges may vary, in certain embodiments a single dosage of an exemplified resveratrol and benzoyl peroxide and/or derivative(s) and/or functionally associated compound(s)-containing formulation of the present invention would contain resveratrol in the range from about 15-1000 milligrams, with 20-334 milligrams or resveratrol representative of the average range needed to be administered orally to the body daily, in combination with about 45-200 mg of a typical oral antibiotic (doxycycline, minocycline, tetracycline), and/or 25-150 mg of spironolactone, and/or 20-100 mg of isotretinoin daily.

In certain embodiments, at least about 1.35 grams of a topical formulation according to the present invention is applied to the affected area of the face (4.5% body surface area), to effectively cover the entire face. It is evident upon review of this specification that the artisan may vary the resveratrol and/or derivative(s) thereof and/or functionally related compound(s) concentration or the benzoyl peroxide and/or its derivative(s) and/or functionally related compound(s) concentration, and/or volume in the topical formulation to manipulate the effective amount of resveratrol and/or derivative(s) thereof and/or functionally related compound(s) and benzoyl peroxide and/or its derivative(s) and/or functionally related compound(s) to be delivered to the patient's face.

In certain embodiments, at least about 300 milligrams of resveratrol is combined with 100 mg of doxycycline in an oral formulation and is administered orally daily. It is evident upon review of this specification that the artisan may vary the resveratrol and/or derivative(s) thereof and/or functionally related compound(s) concentration or the benzoyl peroxide and/or its derivative(s) and/or functionally related compound(s) concentration, and/or volume in the topical formulation to manipulate the effective amount of resveratrol and/or derivative(s) thereof and/or functionally related compound(s) and benzoyl peroxide and/or its derivative(s) and/or functionally related compound(s) to be delivered to the patient's body.

In certain embodiments, the present invention relates to multiple applications/doses of the topical or oral resveratrol and/or derivative(s) thereof and/or functionally related compound(s) in combination with benzoyl peroxide and/or its derivative(s) and/or functionally related compound(s) described in the present invention. Multiple applications will include at least one, two, three, or four doses beyond the initial dose, with one or possibly two additional doses being the most reasonably contemplated.

In certain embodiments, an initial dose is most likely in response to an active state of acne, or other inflammatory or infectious skin disorders as mentioned above, while the additional or subsequent dose(s) are follow up applications to continue to improve, treat, eradicate, or prevent the aforementioned cutaneous disorder. Multiple dosing for a therapeutic regime provides an opportunity to deliver greater amounts of the active ingredients spaced out over a determined time frame.

One aspect of this present invention relates to a method of prophylaxis or prevention of acne or other inflammatory or infectious skin disorders as mentioned above using the resveratrol and/or derivative(s) thereof and/or functionally related compound(s) in combination with benzoyl peroxide and/or its derivative(s) and/or functionally related compound(s). In certain embodiments, a provided composition may be used daily to two or three times daily as a routine regimen. In certain embodiments, at each topical dosing, the formulation is to remain on the skin after application, not to be rinsed, unless in the form of a cleanser, in which case the formulation is to remain on the skin for 30 seconds-5 minutes and then rinsed with warm water. In certain embodiments, for each oral dosing, at least a 2-3 hour time frame is required between subsequent doses.

In certain embodiments, a composition according to the present invention may be delivered topically in one or more forms, non-limiting examples including lotions, creams, ointments, gels, foams, cleansers and the like. In certain embodiments, a composition according to the present invention may be delivered orally in one or more forms, non-limiting examples including pills, syrups, capsules, liquid solutions, powders, or gels.

In certain embodiments, the present invention provides a composition comprising resveratrol and/or derivative(s) thereof and/or functionally related compound(s) and benzoyl peroxide and/or its derivative(s) and/or functionally related compound(s) and a pharmaceutically acceptable carrier, adjuvant, or vehicle.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered, for example, orally or topically. Among acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Pharmaceutically acceptable compositions of this invention may also be administered topically. For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. In certain embodiments, provided compositions should be formulated so that a dosage of between 0.01-100 mg/kg body weight/day of active ingredient(s) can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Figure 2B:
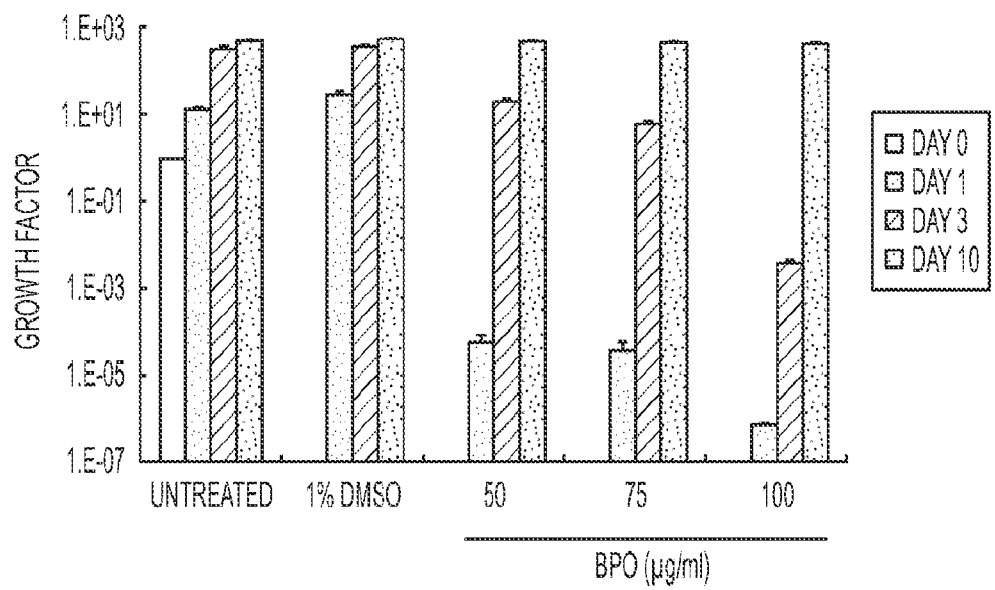
FIG. 2B. Colony Forming Unit (CFU) assays of *P. acnes* incubated with Benzoyl Peroxide (BPO).
Figure 2C:
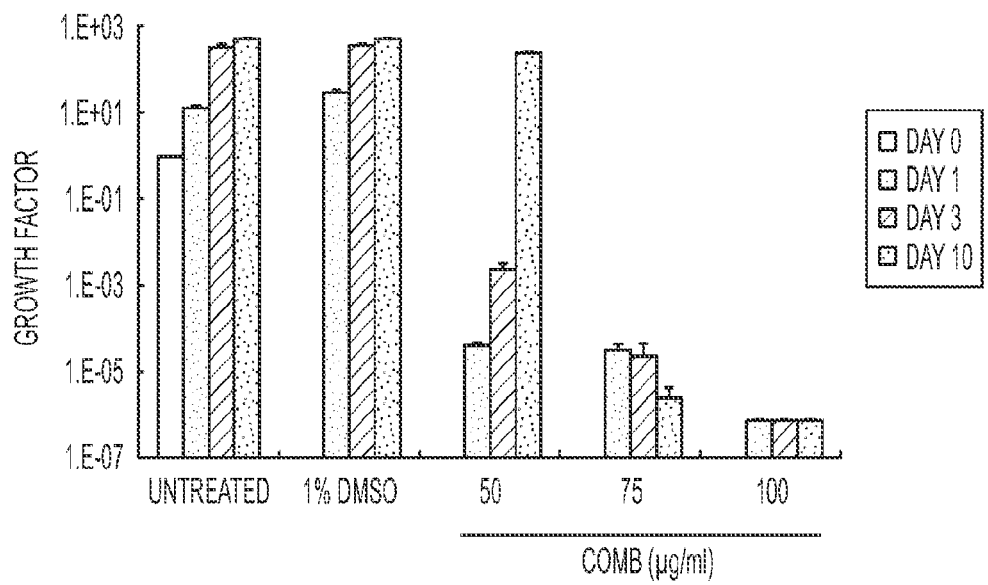
FIG. 2C. Colony Forming Unit (CFU) assays of *P. acnes* incubated with the combination of RES and BPO (COMB).

Specific resveratrol and benzoyl peroxide concentrations tested, as demonstrated in FIGS. 2A, 2B, and 2C include 50 µg/ml, 75 µg/ml, 100 µg/ml of for each experiment consistent of resveratrol, benzoyl peroxide, and combination resveratrol and benzoyl peroxide respectively. The concentration range, shown in FIGS. 2A, 2B and 2C, effectively killed *P. acnes* bacteria, and is presented to exemplify the invention but in no way limits the effective range that may be utilized by the artisan to practice the claimed invention. The artisan may choose an appropriate ranges of resveratrol and/or derivative(s) thereof and/or functionally related compound(s) in combination with benzoyl peroxide and/or its derivative(s) and/or functionally related compound(s) for the active ingredients (measured as weight/volume [w/v]) anywhere from the range of 0.00005 to about 50%.

The w/v ratio of the formulation may be adjusted to be expressed in g/l basis. Adjustments may be easily incorporated with the components resveratrol and/or derivative(s) thereof and/or functionally related compound(s) in combination with benzoyl peroxide and/or its derivative(s) and/or functionally related compound(s) in various concentrations to provide alternate combination formulations for uses disclosed herein.

The artisan will be aware that the percentage by weights of any component may be adjusted to compensate for the concentration of the active ingredient, the texture of the topical formulation (e.g. cream, gel, ointment) and that the components may be added at differing concentrations or may be left out of a formulation or substituted with an equivalent component so as to provide for a resveratrol and/or derivative(s) thereof and/or functionally related compound(s) in combination with benzoyl peroxide and/or its derivative(s) and/or functionally related compound-based topical formulation which possesses efficacy against acne and other inflammatory skin disorders (including but not limited to rosacea, perioral dermatitis, pseudofolliculitis barbae, seborrheic dermatitis) and other infectious skin disease (including but not limited to folliculitis, tinea and onychomycosis) to the exemplified topical formulation described herein.

A person of the ordinary skill in the art will appreciate that the other beneficial agents can be added into a formula of the instant invention. Such beneficial agents include, without limitation antioxidants, vitamins, nutrients, anti-inflammatory agents and the like.

A person of the ordinary skill will have sufficient expertise to properly select the beneficial agent or the combination thereof depending on the specific embodiment of the invention, so that at least one beneficial agent would not negate the beneficial aspects of the formula.

One of ordinary skill in the art will appreciate that the formulations and methods described herein for treating acne and other inflammatory and infectious skin disorders is not intended to be a limiting disclosure, but describes various embodiments of the present invention.

EXEMPLIFICATION

Having described the invention in general terms, the following specific example is offered for purpose of illustration and for illustration only, and no intention to limit the invention is to be inferred there from. A resveratrol (RES) and benzoyl peroxide (BPO) containing formulation for eliminating $P.$ $acnes$ may be prepared as follows. Resveratrol and benzoyl peroxide were obtained from Sigma-Aldrich St. Louis, Mo. They were dissolved separately in DMSO to make stock solutions, diluted to 1% DMSO and then combination treatments resveratrol and benzoyl peroxide were made in concentrations of 50 µg/ml 75 µg/ml, and 100 µg/ml. Antibacterial activity of RES was determined by CFU assays. $Propionibacterium$ $acnes$ ATCC (American Type Cell Culture) strain 6919 was grown anaerobically at 37° C. in Reinforced Clostridial Media (Oxoid) for 3 days and collected in the exponential phase of growth by centrifugation. Bacteria were washed with pH 7 sodium phosphate buffer supplemented by 0.03% Trypticase Soy Media and quantified by reading with a spectrophotometer at 600 nm and applying a conversion of ~1×10$^8$ bacteria=1 absorbance unit. Approximately 1.33×10$^6$ CFUs of bacteria were then added to untreated and DMSO controls, as well as RES, BPO, and combination treatments (25, 50, 75, and 100 µg/mL) in 1 mL Reinforced Clostridial Media. Samples were incubated anaerobically at 37° C. for intervals of 1, 2, 3, 7, and 10 days and then plated on brucella agar with 5% sheep blood supplemented with hemin and vitamin K (Remel). Plates were incubated anaerobically at 37° C. for 3 days, and individual $P.$ $acnes$ colonies were counted to determine antibacterial properties of RES, BPO, and combination treatment. The results were plotted logarithmically as multiples of the initial concentration, which was designated as 1 at Day 0.

Figure 2D:
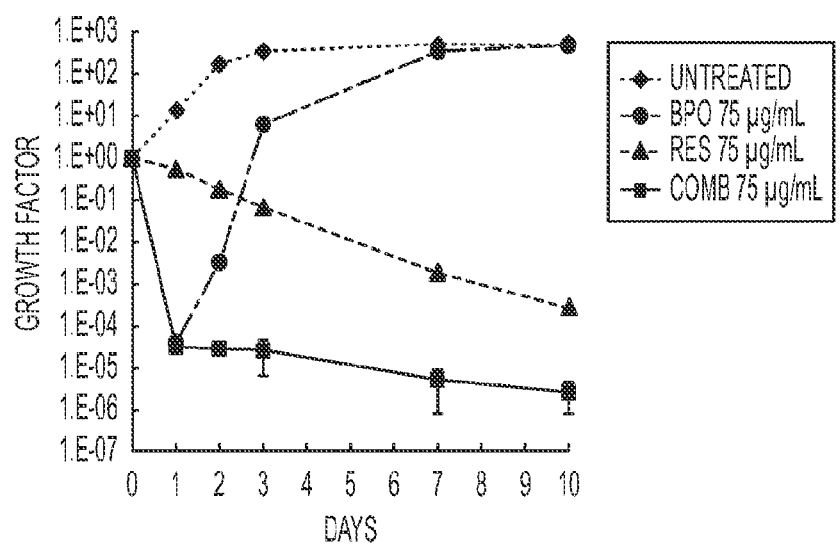
FIG. 2D. Comparison of Colony Forming Unit (CFU) assays of *P. acnes* incubated at equivalent concentrations (75 µg/mL) of RES, BPO, COMB versus control over time. Growth Factor (Y-axis) of *P. acnes* incubated with equivalent concentrations (75 µg/mL) of either RES, BPO, or COMB was compared to control over a 10-day period (X-axis).

The bactericidal activity of resveratrol, benzoyl peroxide, and the combination of resveratrol and benzoyl peroxide are exemplified in FIGS. 2A, 2B, 2C respectively. They are all compared collectively in FIG. 2D, each at a concentration of 75 µg/mL. Similar growth inhibition studies of $P.$ $acnes$ with BPO were performed. Growth inhibition of $P.$ $acnes$ at 50 µg/mL BPO was in the order of 1000× more bactericidal than RES at 24 hours, and BPO activity was also dose dependent (FIG. 2B) with bactericidal activity at doses as low as 25 µg/mL (data not shown). BPO demonstrated different bactericidal kinetics when compared to RES. Surprisingly, BPO had minimal effect on bacterial growth after 24 hours, with $P.$ $acnes$ achieving maximum growth rate by the second day, irrespective of the concentration used. Interestingly, the combination of RES and BPO had an additive and sustained inhibitory effect on the growth and survival of $P.$ $acnes$, most notable at concentrations at and above 50 µg/mL (FIG. 2C). $P.$ $acnes$ plates treated with 1% DMSO alone were comparable in growth to untreated control $P.$ $acnes$ groups. A comparison of RES and BPO alone to the combined RES/BPO treatment group at treatment concentrations of 75 µg/mL highlights the short but immediate bactericidal activity of BPO, the slow but sustained bactericidal activity of RES, and the synergistic bactericidal activity of the RES and BPO combination (FIG. 2D).

Figure 3A:
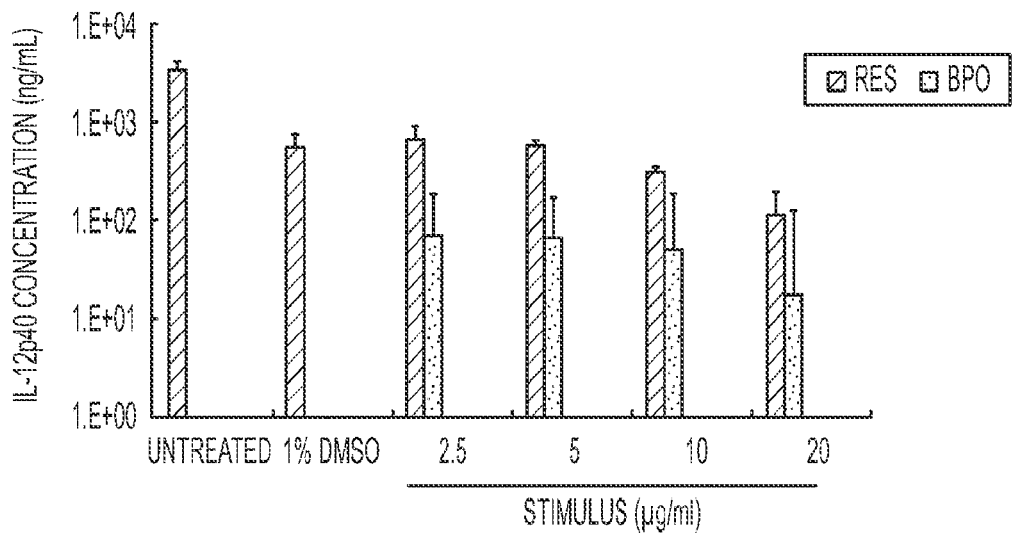
FIG. 3A. Cytokine IL-12 Assay. Concentration of IL-12 (Y-axis) was assessed after primary human monocytes, stimulated with *P. acnes* sonicate, induced IL-12 cytokine secretion in the presence of increasing concentrations of either Resveratrol (RES) or Benzoyl Peroxide (BPO) (X-axis) compared to untreated control and 1% DMSO (solvent for treatments).

The anti-inflammatory properties of resveratrol, benzoyl peroxide and the combination of resveratrol and benzoyl peroxide are exemplified by the cytokine IL-12 assay. (See FIG. 3A) We analyzed the ability of human monocytes stimulated with $P.$ $acnes$ sonicate to secrete IL-12 cytokine when treated with BPO or RES (FIG. 3A). Treatment with 1% DMSO alone also resulted in lower levels of IL-12. Thus, we concluded that only IL-12 levels that were significantly lower than the 1% DMSO treated group could be attributed to RES or BPO. Human monocyte secretion of IL-12 was diminished in the presence of RES at concentrations of 10 µg/mL or more. BPO demonstrated a more potent effect when compared to RES at equivalent concentrations. In the presence of BPO, secreted IL-12 levels were significantly lower than both untreated and RES treated groups, starting at concentrations of 2.5 µg/mL. It is unclear whether IL-12 secretion is BPO dose dependent, as the error bars are broad and overlap significantly between all BPO concentrations. While treatment with DMSO, BPO, or RES could explain the decreased levels of IL-12 measured, a potential confounding factor would be decreased cell viability of the human monocytes. To address this, we next investigated the cytotoxic effects of the various treatment groups.

Figure 3B:
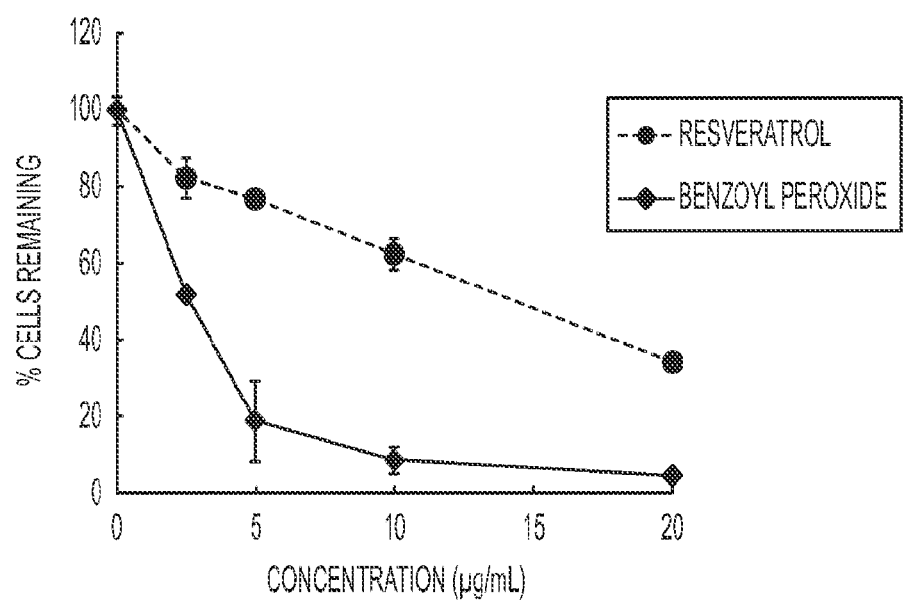
FIG. 3B. Cytotoxicity Assay. Primary human monocytes were incubated with increasing concentrations of Resveratrol (RES) vs. Benzoyl Peroxide (BPO) (X-axis). The percentage of cells still viable after 16 hour incubation (compared to 1% DMSO control) were assessed (Y-axis) by measuring absorbance of the sample, which is proportional to the number of viable cells.

The cytotoxicity of resveratrol, benzoyl peroxide, and the combination of resveratrol and benzoyl peroxide was also assessed. (see FIG. 3B) We analyzed the cell viability of human monocytes using the MTS cytotoxicity assay. Monocyte viability in the presence of RES resulted in dose dependent toxicity, with approximately 35% of monocytes killed at concentrations of 10 µg/mL (FIG. 3B). Monocytes treated with BPO however, resulted in greater than 90% of monocytes killed at 10 µg/mL. Dose-dependent cytotoxicity was not clearly demonstrated by BPO, as evidence by the broad and overlapping error bars at increasing BPO concentrations. The direct cell cytotoxicity of benzoyl peroxide may explain the decrease in IL-12 activity, more a result of direct cell death, than actual anti-inflammatory properties of benzoyl peroxide. The dose dependent cytotoxicity seen with RES however, may explain the decreasing IL-12 levels seen with RES and imply anti-inflammatory properties of RES. Compared at equivalent concentrations, RES was significantly less cytotoxic than BPO. The RES and BPO data was in reference to a 1% DMSO untreated control, which was set at 100% viability.

Figure 4A:
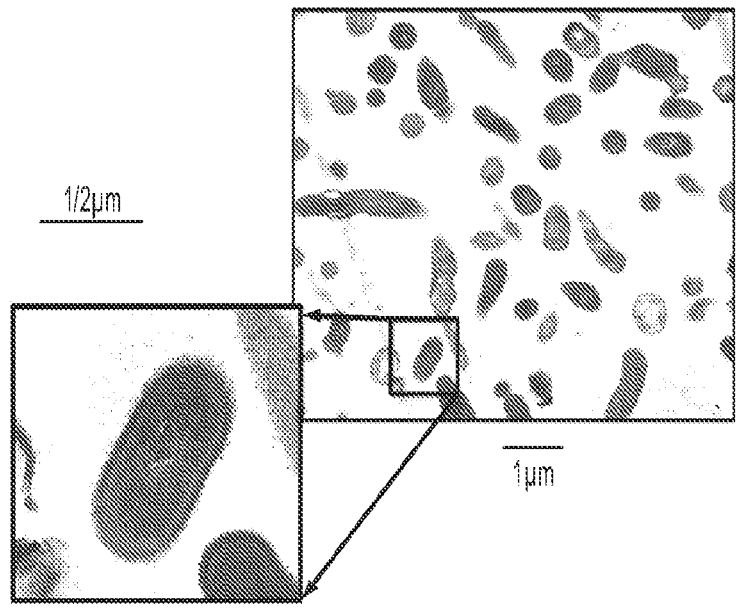
FIG. 4A. Electron Microscopy of *P. acnes* control without stimulus. *Propionibacterium acnes* was incubated without treatment or with 1 mg/mL of RES or BPO for 24 hours. Samples were visualized at 80 kV on a JEOL 100CX electron microscope. Bacteria were magnified according to the scale indicated below the main image, with higher magnification images located in the lower left inset.
Figure 4B:
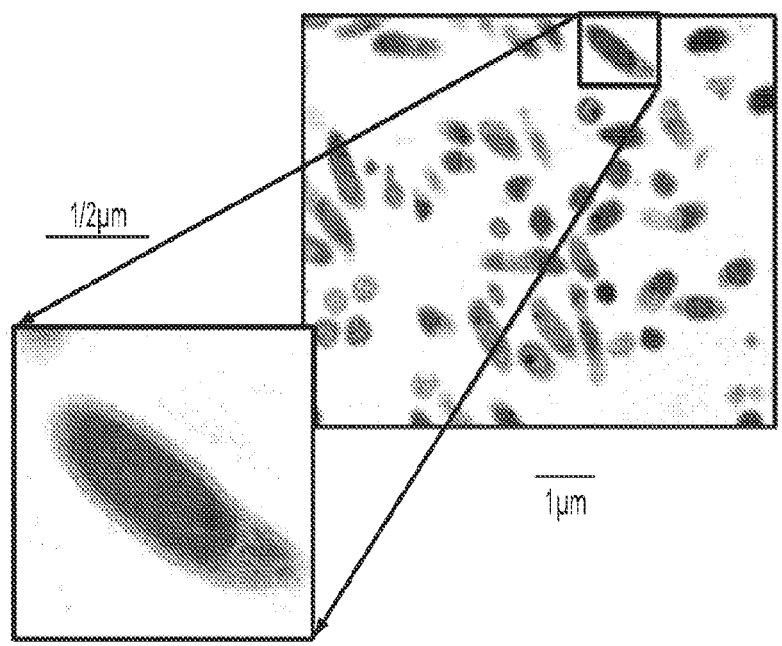
FIG. 4B. Electron Microscopy of *P. acnes* incubated with Resveratrol (RES).
Figure 4C:
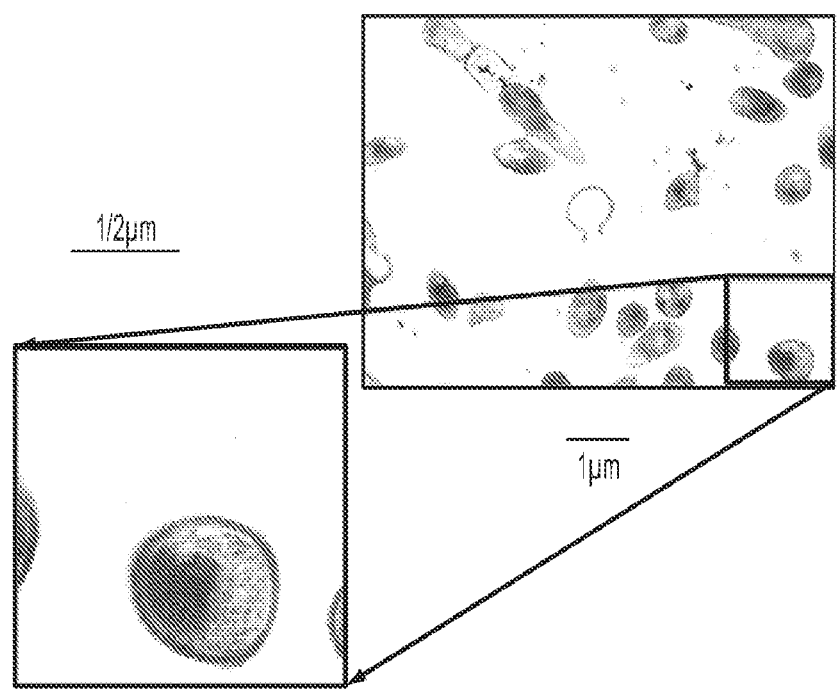
FIG. 4C. Electron Microscopy of *P. acnes* incubated with Benzoyl Peroxide (BPO).

Transmission electron microscopy was performed on *P. acnes* incubated with either RES or BPO for 24 hours. Structural alterations were noted in the bacteria incubated with RES, with loss of membrane definition due to intramembranous edema and loss of well defined extracellular fimbrial structures (FIG. 4B). The bacteria that remained after incubation with BPO (FIG. 4C) were structurally identical to control (FIG. 4A). However the number of bacteria was drastically reduced in the BPO sample, with visible reduction in pellet size prior to resuspension with the PBS and 2% glutaraldehyde solution. This implies cellular lysis and death of the majority of bacterium, leaving only remaining unaffected bacteria to replicate and grow.

Study Data

*P. acnes* Treated with Resveratrol Results in a Sustained and Dose Dependent Bactericidal Effect.

Figure 1B:
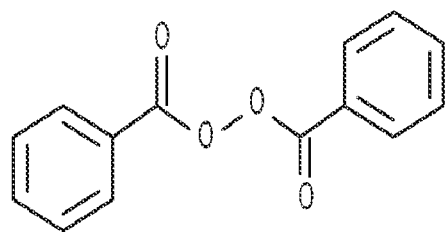
FIG. 1B. Benzoyl Peroxide

To visually demonstrate the effect of RES on *P. acnes* growth, approximately $1.33 \times 10^6$ *P. acnes* bacteria were incubated with increasing concentrations of RES for 48 hours and plated at different dilutions (FIG. 1). Serial dilutions of *P. acnes* plated without treatment provided qualitative comparisons to experimental groups treated with RES. Significant growth inhibition of *P. acnes* was first noted at 50 µg/mL and was dose dependent. Samples treated with 50 µg/mL of RES were found to be approximately equivalent to 1000× dilution of untreated *P. acnes* plates. To determine long-term antimicrobial activity of RES, Colony-Forming-Unit (CFU) assays were then performed over a 10-day period. A sustained and dose dependent bactericidal affect was noted at 75 µg/mL and 100 µg/mL of RES. (FIG. 2A). Our findings suggest that RES reaches a critical concentration between 50 and 75 µg/mL, at which point a threshold for major growth inhibition is passed and RES becomes bactericidal.

*P. acnes* Treated with Benzoyl Peroxide Results in a Short-Term Bactericidal Effect, but a Sustained, Synergistic Bactericidal Effect with Combination RES and BPO Treatment.

Similar growth inhibition studies of *P. acnes* with BPO were performed. Growth inhibition of *P. acnes* at 50 µg/mL was in the order of 1000× more bactericidal than RES at 24 hours, and BPO activity was also dose dependent (FIG. 2B) with bactericidal activity at doses as low as 25 µg/mL (data not shown). BPO demonstrated different bactericidal kinetics when compared to RES. Surprisingly, BPO had minimal effect on bacterial growth after 24 hours, with *P. acnes* achieving maximum growth rate by the second day, irrespective of the concentration used. Interestingly, the combination of RES and BPO had an additive and sustained inhibitory effect on the growth and survival of *P. acnes*, most notable at concentrations at and above 50 µg/mL (FIG. 2C). *P. acnes* plates treated with 1% DMSO alone were comparable in growth to untreated control *P. acnes* groups. A comparison of RES and BPO alone to the combined RES/BPO treatment group at treatment concentrations of 75 µg/mL highlights the short but immediate bactericidal activity of BPO, the slow but sustained bactericidal activity of RES, and the synergistic bactericidal activity of the RES and BPO combination (FIG. 2D).

Human Monocytes Stimulated with *P. acnes* and Treated with Benzoyl Peroxide Results in Lower Levels of IL-12 Secretion Compared to Resveratrol.

We analyzed the ability of human monocytes stimulated with *P. acnes* sonicate to secrete IL-12 cytokine when treated with BPO or RES (FIG. 3A). Treatment with 1% DMSO alone also resulted in lower levels of IL-12. Thus, we concluded that only IL-12 levels that were significantly lower than the 1% DMSO treated group could be attributed to RES or BPO. Human monocyte secretion of IL-12 was diminished in the presence of RES at concentrations of 10 µg/mL or more. BPO demonstrated a more potent effect when compared to RES at equivalent concentrations. In the presence of BPO, secreted IL-12 levels were significantly lower than both untreated and RES treated groups, starting at concentrations of 2.5 µg/mL. It is unclear whether IL-12 secretion is BPO dose dependent, as the error bars are broad and overlap significantly between all BPO concentrations. While treatment with DMSO, BPO, or RES could explain the decreased levels of IL-12 measured, a potential confounding factor would be decreased cell viability of the human monocytes. To address this, we next investigated the cytotoxic effects of the various treatment groups.

Human Monocytes Treated with Benzoyl Peroxide Resulted in Greater Cytotoxicity Compared to Resveratrol.

We analyzed the cell viability of human monocytes using the MTS cytotoxicity assay. Monocyte viability in the presence of RES resulted in dose dependent toxicity, with approximately 35% of monocytes killed at concentrations of 10 µg/mL (FIG. 3B). Monocytes treated with BPO however, resulted in greater than 90% of monocytes killed at 10 µg/mL. Dose-dependent cytotoxicity was not clearly demonstrated by BPO, as evidence by the broad and overlapping error bars at increasing BPO concentrations. The dose dependent cytotoxicity seen with RES however, may explain the decreasing IL-12 levels seen with RES. Compared at equivalent concentrations, RES was significantly less cytotoxic than BPO. The RES and BPO data was in reference to a 1% DMSO untreated control, which was set at 100% viability.

Resveratrol induced structural changes in the cell membrane of *P. acnes*. Transmission electron microscopy was performed on *P. acnes* incubated with either RES or BPO for 24 hours. Structural alterations were noted in the bacteria incubated with RES, with loss of membrane definition due to intramembranous edema and loss of well defined extracellular fimbrial structures (FIG. 4B). The bacteria that remained after incubation with BPO (FIG. 4C) were structurally identical to control (FIG. 4A). However the number of bacteria was drastically reduced in the BPO sample, with visible reduction in pellet size prior to resuspension with the PBS and 2% glutaraldehyde solution. This implies cellular lysis and death of the majority of bacterium, leaving only remaining unaffected bacteria to replicate and grow.

Study Discussion

Resveratrol demonstrated significant in vitro antimicrobial activity against *P. acnes*, the bacteria involved in the pathogenesis of acne, suggesting that it may be a novel therapeutic option or useful adjuvant therapy for the treatment of acne vulgaris in vivo. Interestingly, RES's antimicrobial activity was sustained over time, while BPO's potent bactericidal activity rapidly decreased after 1 day of incubation, at most. RES and BPO in combination had a superior antimicrobial effect that was greater than either compound alone, suggesting that this may be a beneficial combination regimen in the treatment of acne vulgaris. Electron microscopy demonstrated altered bacterial morphology after a 24-hour incubation with RES, with *P. acnes* displaying intramembranous edema and disrupted intracellular structural integrity. This, along with the CFU findings, implies that RES creates a gradual disruption of normal bacterial cellular function, eventuating in cell death over a period of days. This starkly contrasts with BPO, which was found to be strongly bactericidal in the first 24 hours, but with rapidly extinguished activity. This, along with the EM findings of BPO, implies near immediate cellular lysis in the presence of BPO, but little long-term activity.

The anti-inflammatory properties of RES suggested by the IL-12 cytokine assays may be related to direct monocyte toxicity at higher concentrations. The ELISA assay for BPO however, demonstrated no significant difference in IL-12 production at the various treatment concentrations. There was dose dependent cytotoxicity noted on the MTS cytotoxicity assay of BPO, beginning at very low concentrations, indicating that the apparent anti-inflammatory properties of BPO are likely due to direct cell death, and not due to direct reduction of inflammatory mediators.

It should be noted that BPO was toxic to monocytes at concentrations as low as 5 μg/mL, which may explain some of the cutaneous irritation and inflammation found with topical BPO regimens. The toxicity of RES to monocytes is significantly less than BPO, which may translate to decreased irritation in vivo. Since the in vitro antimicrobial activity of RES and BPO in combination was additive, and RES was found to be less cytotoxic than BPO, a combination therapy of RES and BPO may allow for a reduction in the concentration of active compounds, thereby minimizing the cutaneous side effect profile while maximizing the efficacy of topical therapy in vivo, making resveratrol or derivatives thereof and benzoyl peroxide potential novel combination for the treatment of acne vulgaris.

OTHER EMBODIMENTS

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

REFERENCES

1 Del Rosso, J. Q. A 6% benzoyl peroxide foaming cloth cleanser used in the treatment of acne vulgaris: aesthetic characteristics, patient preference considerations, and impact on compliance with treatment. *J Clin Aesthet Dermatol* 2, 26-29 (2009).
2 Yentzer, B. A. et al. An exploratory study of adherence to topical benzoyl peroxide in patients with acne vulgaris. *J Am Acad Dermatol* 60, 879-880, doi:S0190-9622(08) 01450-3 [pii]10.1016/j.jaad.2008.11.019 (2009).
3 Draelos, Z. D. Improving compliance in acne treatment: benzoyl peroxide considerations. *Cutis* 82, 17-20 (2008).
4 Anadolu, R. Y., Sen, T., Tarimci, N., Birol, A. & Erdem, C. Improved efficacy and tolerability of retinoic acid in acne vulgaris: a new topical formulation with cyclodextrin complex psi. *J Eur Acad Dermatol Venereol* 18, 416-421, doi:10.1111/j.1468-3083.2004.00929.x JDV929 [pii] (2004).
5 Egan, N., Loesche, M. C. & Baker, M. M. Randomized, controlled, bilateral (split-face) comparison trial of the tolerability and patient preference of adapalene gel 0.1% and tretinoin microsphere gel 0.1% for the treatment of acne vulgaris. *Cutis* 68, 20-24 (2001).
6 Harper, J. C. An update on the pathogenesis and management of acne vulgaris. *J Am Acad Dermatol* 51, S36-38 (2004).
7 Baur, J. A. & Sinclair, D. A. Therapeutic potential of resveratrol: the in vivo evidence. *Nat Rev Drug Discov* 5, 493-506, doi:nrd2060 [pii] 10.1038/nrd2060 (2006).
8 Baxter, R. A. Anti-aging properties of resveratrol: review and report of a potent new antioxidant skin care formulation. *J Cosmet Dermatol* 7, 2-7 (2008).
9 Docherty, J. J., Smith, J. S., Fu, M. M., Stoner, T. & Booth, T. Effect of topically applied resveratrol on cutaneous herpes simplex virus infections in hairless mice. *Antiviral Res* 61, 19-26 (2004).
10 Chan, M. M. Antimicrobial effect of resveratrol on dermatophytes and bacterial pathogens of the skin. *Biochem Pharmacol* 63, 99-104 (2002).
11 Kedzierski, L., Curtis, J. M., Kaminska, M., Jodynis-Liebert, J. & Murias, M. In vitro antileishmanial activity of resveratrol and its hydroxylated analogues against Leishmania major promastigotes and amastigotes. *Parasitol Res* 102, 91-97 (2007).
12 Jeandet, P. et al. Phytoalexins from the Vitaceae: biosynthesis, phytoalexin gene expression in transgenic plants, antifungal activity, and metabolism. *J Agric Food Chem* 50, 2731-2741 (2002).
13 Sen, C. K. et al. Oxygen, oxidants, and antioxidants in wound healing: an emerging paradigm. *Ann N Y Acad Sci* 957, 239-249 (2002).
14 Calabrese, G. Nonalcoholic compounds of wine: the phytoestrogen resveratrol and moderate red wine consumption during menopause. *Drugs Exp Clin Res* 25, 111-114 (1999).
15 Gehm, B. D., McAndrews, J. M., Chien, P. Y. & Jameson, J. L. Resveratrol, a polyphenolic compound found in grapes and wine, is an agonist for the estrogen receptor. *Proc Natl Acad Sci USA* 94, 14138-14143 (1997).
16 Fabbrocini, G. et al. Resveratrol-containing gel for the treatment of acne vulgaris: a single-blind, vehicle-controlled, pilot study. *Am J Clin Dermatol* 12, 133-141, doi:5 [pii] 10.2165/11530630-000000000-00000.
17 Docherty, J. J., McEwen, H. A., Sweet, T. J., Bailey, E. & Booth, T. D. Resveratrol inhibition of *Propionibacterium acnes*. *J Antimicrob Chemother* 59, 1182-1184 (2007).
18 Slaga, T. J. Inhibition of the induction of cancer by antioxidants. *Adv Exp Med Biol* 369, 167-174 (1995).
19 Valacchi, G., Rimbach, G., Saliou, C., Weber, S. U. & Packer, L. Effect of benzoyl peroxide on antioxidant status, NF-kappaB activity and interleukin-1alpha gene expression in human keratinocytes. *Toxicology* 165, 225-234, doi:S0300483X01004309 [pii] (2001).
20 Bonnetblanc, J. M. & Bernard, P. Benzoyl peroxide in seborrheic dermatitis. *Arch Dermatol* 122, 752 (1986).
21 Bonnetblanc, J. M., De Prost, Y., Bazex, J. & Maignan-Gayrard, P. [Treatment of seborrheic dermatitis with benzoyl peroxide]. *Ann Dermatol Venereol* 117, 123-125 (1990).
22 Montes, L. F., Cordero, A. A., Kriner, J., Loder, J. & Flanagan, A. D. Topical treatment of acne rosacea with benzoyl peroxide acetone gel. *Cutis* 32, 185-190 (1983).
23 Ozturkcan, S., Ermertcan, A. T., Sahin, M. T. & Afsar, F. S. Efficiency of benzoyl peroxide-erythromycin gel in comparison with metronidazole gel in the treatment of acne rosacea. *J Dermatol* 31, 610-617, doi:031080610 [pii] (2004).

24 Poli, F., Prost, C. & Revuz, J. [Gram-negative bacteria folliculitis]. *Ann Dermatol Venereol* 115, 797-800 (1988).

25 Eady, E. A. & Cove, J. H. Topical antibiotic therapy: current status and future prospects. *Drugs Exp Clin Res* 16, 423-433 (1990).

26 Prestia, A. E. Topical benzoyl peroxide for the treatment of tinea versicolor. *J Am Acad Dermatol* 9, 277-278 (1983).

27 Kligman, A. M., Leyden, J. J. & Stewart, R. New uses for benzoyl peroxide: a broad-spectrum antimicrobial agent. *Int J Dermatol* 16, 413-417 (1977).

28 Elsaie, M. L., Abdelhamid, M. F., Elsaaiee, L. T. & Emam, H. M. The efficacy of topical 2% green tea lotion in mild-to-moderate acne vulgaris. *J Drugs Dermatol* 8, 358-364 (2009).

29 Grandinetti, P. J. & Fowler, J. F., Jr. Simultaneous contact allergy to neomycin, bacitracin, and polymyxin. *J Am Acad Dermatol* 23, 646-647 (1990).

30 Patel, M., Bowe, W. P., Heughebaert, C. & Shalita, A. R. The development of antimicrobial resistance due to the antibiotic treatment of acne vulgaris: a review. *J Drugs Dermatol* 9, 655-664.

31 Kinney, M. A., Yentzer, B. A., Fleischer, A. B., Jr. & Feldman, S. R. Trends in the treatment of acne vulgaris: are measures being taken to avoid antimicrobial resistance? *J Drugs Dermatol* 9, 519-524.

We claim:

1. A topical formulation comprising resveratrol or trans-3,4',5 trihydroxystilbene (trans-resveratrol) at a concentration from about 0.05% (w/v) to about 20% (w/v), and benzoyl peroxide at a concentration from about 0.05% (w/v) to about 20% (w/v).

2. The topical formulation of claim 1, wherein the formulation comprises resveratrol at a concentration from about 0.05% (w/v) to about 20% (w/v), and benzoyl peroxide at a concentration from about 2.5% (w/v) to about 20% (w/v).

3. The topical formulation of claim 1, wherein the formulation comprises trans-3,4',5 trihydroxystilbene (trans-resveratrol) at a concentration from about 0.05% (w/v) to about 20% (w/v), and benzoyl peroxide at a concentration from about 2.5% (w/v) to about 20% (w/v).

4. The topical formulation of claim 1, further comprising an antioxidant.

5. The topical formulation of claim 4, wherein the antioxidant is ascorbic acid (vitamin C), α-tocopherol (Vitamin E), a polyphenol, lipoic acid, glutathione, uric acid, a carotene, ubiquinol (coenzyme Q), green tea extract, or coffee berry extract.

6. The topical formulation of claim 1, further comprising a solubilizer wherein the solubilizer comprises a water miscible organic compound.

7. The topical formulation of claim 1, further comprising a solubilizer phase consisting essentially of one or more surfactants.

8. The topical formulation of claim 1, further comprising a suspending agent, wherein said suspending agent is selected from the group consisting of olive oil, shea butter, cocoa butter, vegetable oil, and combinations thereof.

9. The topical formulation of claim 1, further comprising a non-ionic surfactant, wherein said non-ionic surfactant is oleyl alcohol, lanolin alcohol, acetylated lanolin alcohol, cetyl alcohol, stearyl alcohol, cetostearyl alcohol, oleyl alcohol, polyethylene glycol (PEG), polypropylene glycol, glucoside alkyl ethers, triton X-100, glycerol alkyl esters, or sorbitan.

10. The topical formulation of claim 1, further comprising a preservative, tinosan, potassium sorbate, grapefruit seed extract, a paraben compound, or a combination thereof.

11. The topical formulation of claim 1, further comprising an emulsifier, wherein said emulsifier is stearyl alcohol, polysorbate 60, steareth-20, or Irish moss.

12. The topical formulation of claim 1, further comprising an emollient, wherein said emollient is candelilla wax, sweet almond oil, apricot oil, emu oil, argan oil, glycerin, coconut oil, grape seed oil, honey, or lanolin.

13. The topical formulation of claim 1, further comprising a fragrance.

14. A method of treating acne which comprises topically administering a topical formulation of claim 1 to a patient in need thereof.

15. The method of claim 14, wherein the topical formulation is administered to the patient as a single dose.

16. The method of claim 14, wherein the topical formulation is administered to an affected area selected from the group consisting of the face, back, chest, arms, neck, and buttocks of the patient, or any combination thereof.

17. The method of claim 14, wherein the acne is caused by *Propionibacterium acnes*.

18. A method of treating a skin condition which comprises topically administering a topical formulation of claim 1 to a patient in need thereof.

19. The method of claim 18, wherein the topical formulation is administered to the patient as a single dose.

20. The method of claim 18, wherein the topical formulation is administered to an affected area selected from the group consisting of the face, back, chest, arms, neck, and buttocks of the patient, or any combination thereof.

21. The method of claim 19, wherein the skin condition is caused by *Propionibacterium acnes*.

* * * * *